United States Patent

Rosenberg

[19]

[11] Patent Number: 6,063,094
[45] Date of Patent: May 16, 2000

[54] ADJUSTABLE SKIN MESHER DEVICE AND A SYSTEM FOR USING THE SAME

[75] Inventor: Lior Rosenberg, Omer, Israel

[73] Assignee: L.R. Surgical Instruments Ltd., Ofakim, Israel

[21] Appl. No.: 09/077,269

[22] PCT Filed: Dec. 6, 1996

[86] PCT No.: PCT/IL96/00174

§ 371 Date: Aug. 3, 1998

§ 102(e) Date: Aug. 3, 1998

[87] PCT Pub. No.: WO97/20509

PCT Pub. Date: Jun. 12, 1997

[30] Foreign Application Priority Data

Dec. 7, 1995 [IL] Israel ......................................... 116282

[51] Int. Cl.[7] .................................................. A61B 17/50
[52] U.S. Cl. ............................................ 606/132; 83/678
[58] Field of Search ................................. 606/132; 83/678

[56] References Cited

U.S. PATENT DOCUMENTS

| | | | |
|---|---|---|---|
| 3,470,782 | 10/1969 | Acker | 83/451 |
| 3,866,497 | 2/1975 | Wolfberg et al. | 83/678 |
| 3,978,752 | 9/1976 | Meaden et al. | 83/678 |
| 3,978,753 | 9/1976 | Meaden et al. | 83/678 |
| 5,196,020 | 3/1993 | Atkinson et al. | 606/132 |
| 5,219,352 | 6/1993 | Atkinson | 606/132 |

*Primary Examiner*—Michael H. Thaler
*Attorney, Agent, or Firm*—Cowan, Liebowitz & Latman, P.C.; William H. Dippert

[57] ABSTRACT

The present invention generally relates to a skin graft preparation device, or mesher. This device is designed to incise and "mesh" a piece of skin, usually prior to grafting to allow it to expand and cover an area larger than its donor site area. More specifically, the invention relates to an adjustable mesher device wherein the mesher has an adjustable meshing drum (roller) or drums useful for the meshing of the entire range of meshing ratios, thus eliminating the need to keep various meshing devices. Another embodiment of the mesher has two consecutive meshing drums. A further embodiment of the mesher has a rotatable common holder allowing selection from a number of meshing drums. These meshers can mesh skin in both powered and manual modes of operation and may be used with most existing graft carriers or may be used without any carrier. The present invention further relates to a system for using the mesher.

45 Claims, 13 Drawing Sheets

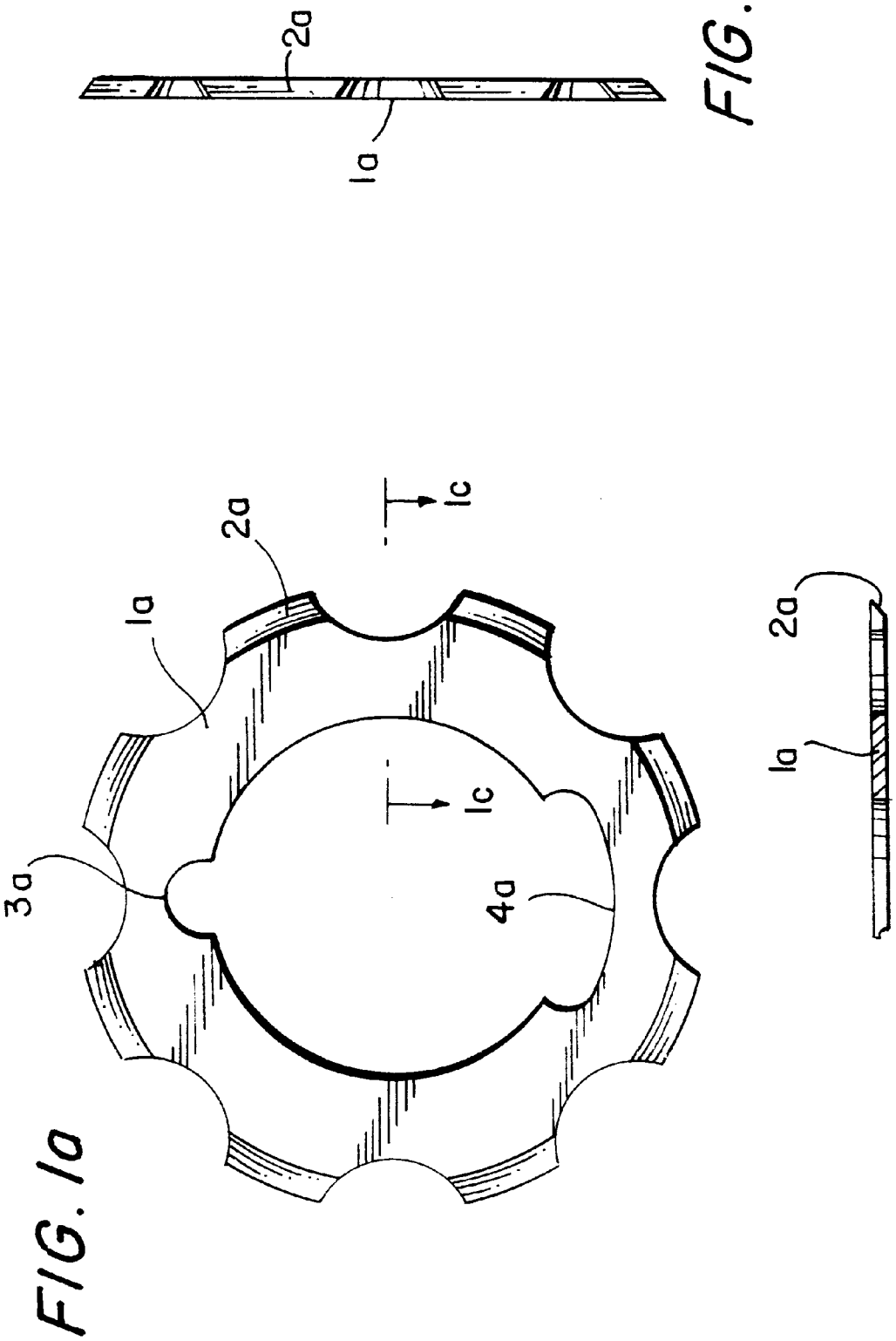

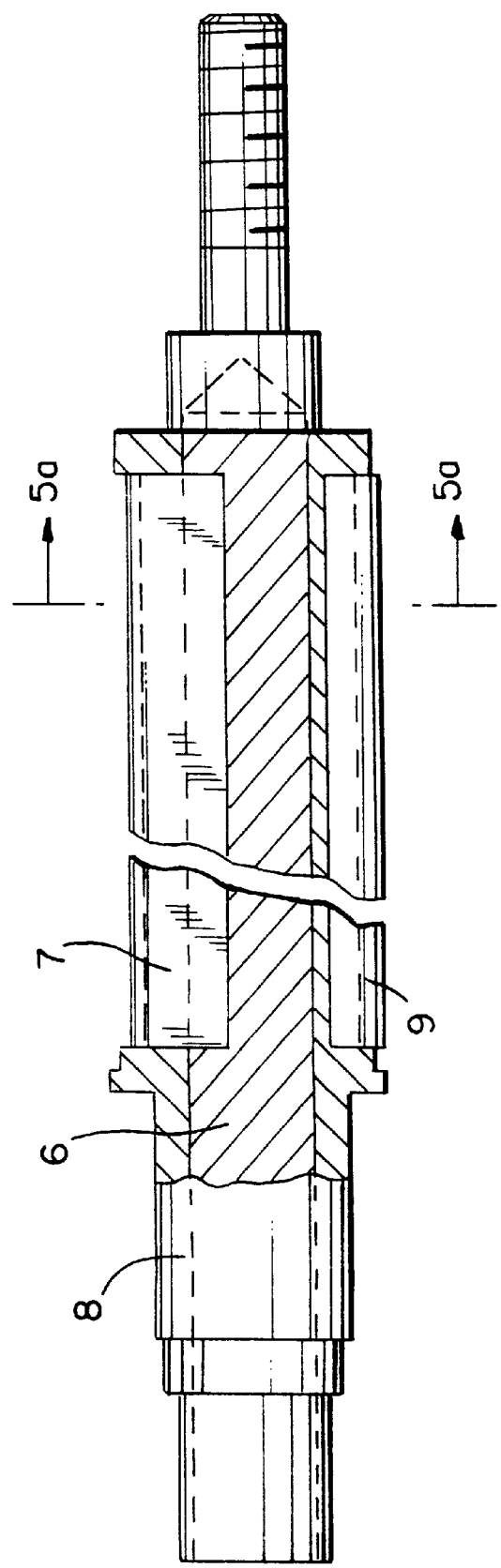

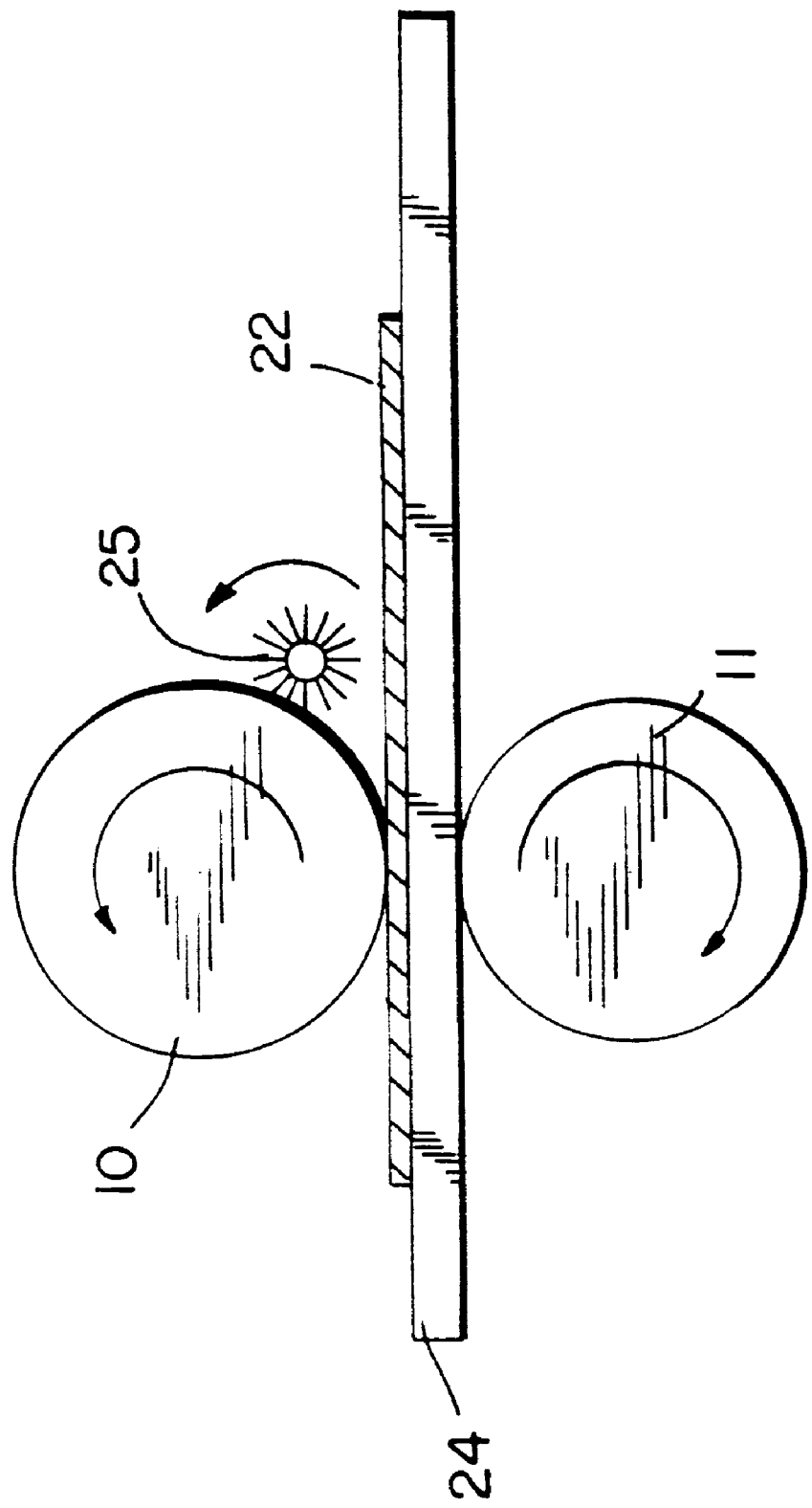

ADJUSTABLE SKIN MESHER DEVICE AND A SYSTEM FOR USING THE SAME

FIELD OF THE INVENTION

The present invention generally relates to a skin graft preparation device, hereinafter called a mesher. This device is designed to incise and "mesh" a piece of skin usually prior to grafting in order to allow it to expand and cover a larger area than its donor site area. More specifically the said invention relates to an adjustable mesher device wherein the mesher has an adjustable meshing drum (roller) or drums useful for the meshing of the entire range of meshing ratios thus eliminating the need to keep various meshing devices. Another embodiment of the mesher has two consecutive meshing drums. A further embodiment of the mesher has a rotatable common holder allowing selection from a number of meshing drums. These meshers can mesh skin in both powered and manual modes of operation and may be used with most existing skin graft carriers or may be used without any carrier. The present invention further relates to a system for using the mesher.

BACKGROUND OF THE INVENTION

Skin graft meshers are designed to incise and "mesh" a piece of skin prior to grafting in order to allow it to expand and cover a larger area than its donor site area. The large number of incisions offer a good drainage to exudate from the recipient site but may leave, after healing and complete epithelialization, a typical "mesh" pattern that is directly dependent on the incisions size and on the pattern. The skin grafts may be meshed into several mesh ratios according to needs, available skin, functional, and aesthetic considerations. The commonest ratios are 1:1.5 and 1:3, and different cutting devices and systems are available respectively.

The length and width of the meshed skin graft is limited to the available carrier's dimensions, usually 30×10 cms. The old type meshing devices (U.S. Pat. No. 3,613,242) includes a planar skin graft cutter.

The typically modern up-to-date meshing system includes a mesher containing cutting drum (roller) and skin graft carriers. The carriers are compatible only to the specific mesher. Thus, in order to have the entire range of meshing ratios, one should keep "meshing systems" that include stocks of different skin graft carriers with the compatible mesher or different ratio cutting drums or meshers with compatible carriers. (U.S. Pat, Nos. 5,004,468 and 5,219, 352)

Conventionally the meshing work is done by cranking a long ratchet or a crank which demands rather strenuous work by the nurse or the surgeon and interferes with the fine control of the extruded skin graft, as at least two people are needed to operate the mesher and to control the skin graft.

The adjustable mesher of the present invention solves the aforementioned disadvantages associated with the meshing of skin. The adjustable mesher offers in a single skin mesher all of the range of skin meshing ratios. The adjustable mesher omits the stocks of different skin graft carriers. It may accommodate any existing carrier or cutting board or it can be used without a carrier at all. Furthermore the adjustable mesher can mesh skin in both powered and manual modes of operation, and is easy to operate.

SUMMARY OF THE INVENTION

The present invention provides an adjustable skin graft preparation device for producing a predetermined pattern of incisions comprising of: an upper or lower meshing drum or drums holding a plurality of pairs of annular cutting disks or holding a plurality of single annular cutting disks and the said cutting disks have adjustable predetermined angular orientation one to the other on the same drum and between drums when there is more than one meshing drum, an upper or lower feeding drum or drums, means for setting and locking the cutting disks on the meshing drum or drums, means for rotating the drums, means for controlling the space between the meshing drum or drums and the feeding drum or drums for feeding variable thickness skin carrier plates or cutting boards or for feeding skin graft samples directly between the drums, and a geared linkage mechanism wherein the synchronous rotation of the meshing drum or drums and the feeding drum or drums is maintained over a range of skin carrier plate width s for skin graft samples or for skin carrier plates or for cutting boards of thicknesses from 0.0 mm to approximately 15.0 mm. The present invention also provides an adjustable skin graft preparation device wherein the meshing drum or drums can be two or three parallel different ratio meshing drums connected to a common holder wherein the rotation of the holder fixes into operating position the required appropriate drum.

The present invention furthermore provides in one of its preferred embodiment an adjustable skin graft preparation device wherein the meshing drum or drums can be two different consecutive parallel meshing drums and wherein the distance between the two different consecutive parallel meshing drums or the relative rotational phase between the two different consecutive parallel meshing drums can be set and locked, thereby determining an incision characteristic of the pattern. In another preferred embodiment, the present invention provides an adjustable skin graft preparation device comprising of a meshing drum (preferably the upper drum) holding a plurality of pairs of annular cutting disks, a feeding drum (preferably the lower drum), means for setting and locking the angular orientation of the cutting disks in each pair of cutting disks on the meshing drum, means for rotating the drums, means for controlling the space between the two drums for feeding variable thickness skin carrier plates or cutting boards or for feeding skin graft samples directly, a geared linkage mechanism wherein the synchronous rotation of the upper and lower drums is maintained over a range of skin carrier plate acceptance angles for skin graft samples or for skin carrier plates or for cutting boards of samples or for skin carrier plates or for cutting boards of thicknesses from 0.0 mm to approximately 15.0 mm, and a linkage mechanism that may allow connecting extended electric power to the geared rotation mechanism of the drums.

The present invention further provides a meshing system comprising of a mesher device, a closed carrying and autoclaving container for the mesher device, an electric motor unit which is adapted to the said container and which may be inserted into and thus located inside said container, and a rotatable drive shaft coupling that is an integral part of said container for aseptically transferring the rotation power from the electric motor unit to the mesher device drums. The electric motor unit contains an electric motor, a means for transferring the rotational energy between the electric motor's rotor and a rotatable drive shaft, and an adequate source of power such as a battery or an AC 220-110 V source, or an adequate DC source.

In the meshing system the mesher device is fixed on the container's cover and connected at its bottom to a rotatable drive shaft coupling that is an integral part of said cover providing the rotation power from the electric motor unit to the meshing device and the rotation power is transferred from the rotatable drive shaft coupling to the meshing device's drums through several toothed wheels.

The present invention further provides that the closed carrying and autoclaving container for the mesher device, or for other medical devices, is an autoclavable sealable container for use in sterile operation room environments. On the container's cover there is a rotatable drive shaft coupling for mechanical connection with the electric motor unit for operating mechanical devices placed on the container's cover.

The present invention further provides a meshing system wherein sterilization and aseptic techniques are applied to the meshing device and to the container so that the said system can be used in sterile environments such as medical operating rooms and the operating room's aseptic environment is protected by the sterile container from contamination from the non-sterile power unit inside the container.

DETAILED DESCRIPTION OF THE INVENTION

The adjustable mesher device, according to the present invention, solves many of the problems which are associated with the existing skin meshing devices. The adjustable mesher device according to the present invention offers, in a single skin mesher, all of the range of skin meshing ratios. Furthermore the adjustable mesher omits the stocks of different skin graft carriers and can mesh skin in both powered and manual modes of operation.

The adjustable mesher device according to the present invention contains one or more meshing drums which allows the skin to be meshed in the entire range of meshing ratios. These drums eliminate the need to keep various meshing devices. Also the adjustable meshing drum allows different ratios to be chosen for the same skin graft piece or for consecutive pieces.

The present invention provides an adjustable skin graft preparation device for producing a predetermined pattern of incisions comprising of: an upper or lower meshing drum or drums holding a plurality of pairs of annular cutting disks or holding a plurality of single annular cutting disks and the said cutting disks have adjustable predetermined angular orientation one to the other on the same drum and between drums when there is more than one meshing drum, an upper or lower feeding drum or drums, means for setting and locking the cutting disks on the meshing drum or drums, means for rotating the drums, means for controlling the space between the meshing drum or drums and the feeding drum or drums for feeding variable thickness skin carrier plates or cutting boards or for feeding skin graft directly between drums, and a geared linkage mechanism wherein the synchronous rotation of the meshing drum or drums and the feeding drum or drums is maintained over a range of skin carrier plate acceptance angles for skin graft samples or for skin carrier plates or for cutting boards of thicknesses from 0.0 mm to approximately 15.0 mm.

An acceptance angle for a 0.0 mm thick carrier plate indicates a case where the skin graft sample is feed directly into the mesher device. A thin film disposable plate or a thin film disposable envelope would be thin enough to pass through the 0.0 mm setting, sufficiently rigid to pass through between the rotating drums, and sufficiently soft so as to be incised with the same meshing pattern as the skin graft sample that it carries. Alternately the feeding drum or drums could each be enclosed in a thin disposable soft resilient tube to accommodate the direct feeding of skin graft samples.

The present invention also provides an adjustable skin graft preparation device wherein the meshing drum can be comprised of two or three parallel different ratio meshing drums connected to a common holder wherein the rotation of the holder fixes into operating position the required appropriate drum.

The present invention also provides an adjustable skin graft preparation device wherein the meshing drum or drums can be comprised of two different consecutive parallel meshing drums. For example where the upper drum is comprised of two consecutive parallel drums one after the other for creating a predetermined composite meshing pattern wherein each drum contributes in turn a portion of the requisite incisions. Setting and locking the distance between the two different consecutive parallel meshing drums determines an incision characteristic of the pattern and/or the relative rotational phase between two different consecutive parallel meshing drums can be set and locked to determine an incision characteristic of the pattern.

The present invention also provides an adjustable skin graft preparation device comprising of an upper meshing drum (hereinafter called the upper drum) holding a plurality of pairs of annular cutting disks, a lower feeding drum (hereinafter called the lower drum), means for setting and locking the angular orientation of the cutting disks in each pair of cutting disks on the upper drum, means for rotating the drums, means for controlling the space between the two drums for feeding variable thickness skin carrier plates or cutting boards or for feeding skin graft samples directly, a geared linkage mechanism wherein the synchronous rotation of the upper and lower drums is maintained over a range of skin carrier plate acceptance angles for skin graft samples or for skin carrier plates or for cutting boards of thicknesses from 0.0 mm to approximately 15.0 mm, and a linkage mechanism that may allow connecting extended electric power to the geared rotation mechanism of the drums.

The present invention further provides a meshing system comprising of a mesher device, a closed carrying and autoclaving container for the mesher device, an electric motor unit which is adapted to the said container and which may be inserted into and thus located inside said container, and a rotatable drive shaft coupling that is an integral part of said container for aseptically transferring the rotation power from the electric motor unit to the mesher device drums.

In the meshing system the mesher device is fixed on the container's cover and connected at its bottom to a rotatable drive shaft coupling that is an integral part of said cover and providing the rotation power from the electric motor unit to the meshing device and the rotation power is transferred from the rotatable drive shaft coupling to the meshing device's drums through several toothed wheels.

The present invention further provides that the completely closed carrying and autoclaving container for an adjustable skin graft preparation device, or for other medical devices, is an autoclavable sealable container for use in sterile environments such as medical operating rooms. Sterilization techniques are applied to the meshing device and to the container so that the said system can be used in sterile environments such as medical operating rooms and the operating room's aseptic environment is protected by the sterile container from contamination from the non-sterile power unit inside the container.

On the container's cover there is a rotatable drive shaft coupling for mechanical connection with the electric motor unit for operating mechanical devices placed on the container's cover.

The adjustable mesher device according to the present invention contains an adjustable meshing drum. This drum holds a plurality of pairs of cutting disks. Each cutting disk in the pair is an annulus, with a flat side and a curved or beveled other side, whose external circumference is comprised of a symmetric series of cutting blades, the flat cutting edge of which is pressed to the flat cutting edge of the respective paired disk. The internal circumference of each cutting disk contains two notche s, one narrow and one wide.

There are two differences between the two disks in each pair of cutting disks on the adjustable meshing drum, (a) their flat sides are placed one against the other and (b) the angular orientation between the external blades and the internal notches is reversed wherein on the one disk the centers of internal notchs are between respective consecutive blades and on the other disk the centers of internal notchs are aligned with the centers of respective blades.

The meshing drum maintains the angular orientation between the two disks in each pair of disks by the way that the drum grasps each disk in the pair relative to the other disk. On the entire length on the drum there are two tracks. One track is fixed in its place and cannot move while the other track can pivot along the entire length of the drum. These two tracks fit into the two notches in the internal circumference of the annular cutting disks.

According to the present invention a means for setting the angular orientation and locking the plurality of the paired cutting disks are two tracks located along the upper drum wherein one track is fixed in the drum for locking one disk in every pair of disks in its place and this track cannot move while the other track can pivot along the entire length of the drum and this pivoting slightly rotates one disk in every pair of disks and this pivoting is for changing the angular orientation of the other disk in every pair.

Each pair of disks is placed on the pair of tracks of the meshing drum such that the fixed track passes through the wide notch of one disk and the narrow notch of the other disk in the pair and the pivoting track passes through the other available notch on each disk.

Setting the angular orientation between the two disks in each par of disks is accomplished by pivoting the track to a predetermined angle which slightly rotates and thus changes the relative position of the narrow internal notch on each disk with respect to the wide internal notch on its mate and likewise changes both the length of the paired blades on the external circumference of the cutting disk and the length of the spaces between paired blades. After simultaneously setting the angular orientation of one disk in each pair of disks for all of the pairs of disks by changing the track to meshing drum angle of the entire pivoting track, the angle is locked in place for use.

Thus, setting the pivot angle of the track on the drum modulates the degree of the external circumference of the disk pair which is cutting blade and that which is space between blades . Each incision made on the skin graft sample then comes from an effective cutting blade which has a blade contribution from one or both of the cutting disks in the pair.

The rotation of the upper drum over a piece of skin directly or over the moving carrier plate or over the moving cutting board produces a predetermined incision series whose incision length to incision skip ratio determines the mesh ratio and the fact that the length of the upper drum contains a plurality of single matched adjustable pairs of cutting disks produces the actual predetermined pattern of incisions on the skin graft sample.

Thus a piece of skin directly or on a carrier plate or on a cutting board passing between the upper drum and the lower drum is incised by the cutting disks in a predetermined pattern of incisions according to the angular orientation of the cutting disks in each pair of cutting disks or according to the blade distribution on the individual cutting disks.

An adjustable skin graft preparation device according to the present invention can have a fixed comb or a rotating brush or a drum or a serrated drum, being parallel and along side of the meshing drum or drums, for detaching the meshed skin graft from the meshing drum before the said skin becomes wrapped onto the meshing drum and for spreading the said skin onto the carrier plate or cutting board.

The adjustable mesher device according to the present invention allows any smooth plate (thickness range from 0.0 mm. to 15 mm.) to be used as a skin graft carrier or may be used without any carrier. The means controlling the space between the meshing and the feeding drums are micrometric screw or screws or one or two eccentric axles or wheels which allow the raising or lowering of the drum or drums.

The longer and wider size of the adjustable mesher's skin graft carrier aperture accommodates any size of donated skin and irregular shapes of the skin for grafting are also accommodated. The device is eliminating the need to keep stocks of different carriers for different meshing devices for different meshing ratios. The skin graft sample or the carrier plate or the cutting board passes between the upper drum and the lower drum.

The present invention further relates to a unique autoclavable closed carrying and autoclaving container for the adjustable mesher. This container offers the option of adding, using sterilization and aseptic techniques, a power pack unit. It is the power pack unit that transforms the adjustable mesher into a powered adjustable skin meshing device. The power pack unit may be located in the container.

The power pack unit is an electric motor unit wherein is contained an electric motor, a coupling for the transfer of rotational energy between the electric motor's rotor and a rotatable drive shaft, an adequate source of power such as a battery or an AC 220-110 V source, or an adequate DC source.

The electric motor unit may be a non-sterile motor unit which may be transferred to and locked into the container using aseptic techniques.

This unique feature, a power pack unit, allows for a comfortable, accurate, and effortless meshing of any quantity of skin grafts by a single operator. The option of using the adjustable mesher in a manual mode of operation is preserved for emergency situations, such as power outage s, where the mesher drums are rotated by manually cranking a ratchet. Another embodiment of the present invention provides a device wherein the means for setting the angular orientation and locking the plurality of single cutting disks are two tracks located along each meshing drum wherein one track is fixed in the drum for locking one or more of the disks in its place and this track cannot move while the other track can pivot along the entire length of the drum and this pivoting slightly rotates the remaining disks and this pivoting is for changing the angular orientation of the one or more disks on the meshing drum or drums with respect to the remaining disks on the upper drum.

Each annular cutting disk in the plurality of single cutting disks has a symmetric series of blades on the external circumference and a wide notch and a narrow notch are located on the internal circumference for the insertion of the meshing drum's tracks.

A plurality of single disks is placed on the pair of tracks of the meshing drum such that the fixed track passes through the wide notch of one or more disks and the narrow notch of the remaining disks, and the pivoting track passes through the other available notch on each disk. The relative orientational phase between one or more of the cutting disk in the plurality of single disks and the remaining disks is fixed by setting the pivoting track on the meshing drum to a predetermined angle.

The present invention will be further described by FIGS. 1 12. These figures are solely intended to illustrate the preferred embodiment of the invention and are not intended to limit the scope of the invention in any manner.

BRIEF DESCRIPTION OF THE FIGURES

FIG. 4 illustrates a longitudinal cross section of the upper drum composite axle (without the cutting disks).

FIG. 13 illustrates a profile of a skin detaching rotating brush or a soft serrated cylinder in juxtaposition to a meshing drum.

DETAILED DESCRIPTION OF THE FIGURES

Figures 1, 12A:
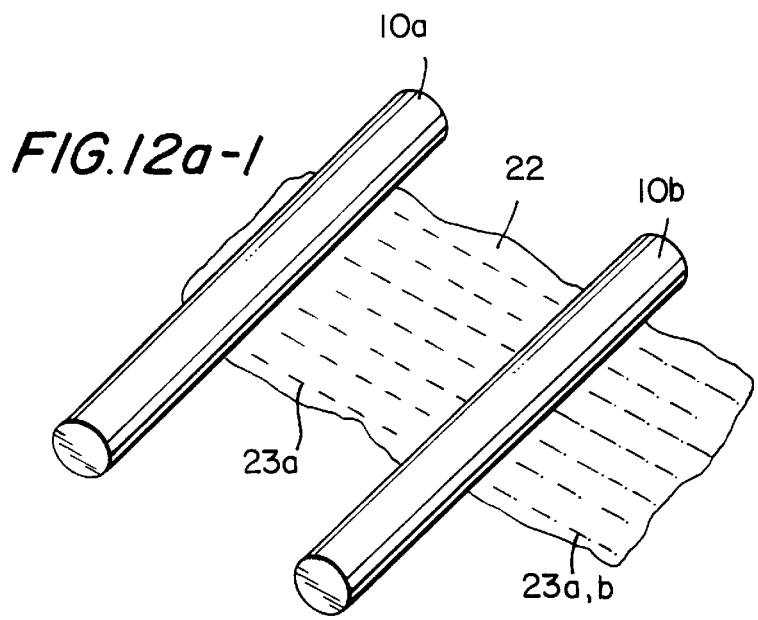
FIG. 1 illustrates a side view of a type "A" cutting disk.
FIGS. 12a and 12b illustrate two oblique views of the incision contributions to a composite meshing pattern as may be produced by a mesher device as illustrated in FIG. 11.

FIG. 1 illustrates a side view of a type "A" cutting disk. The type "A" cutting disk (1a) is a thin annular disk whose external circumference is comprised of a symmetric series of cutting blades (2a). The internal circumference of the cutting disk contains two diametrically opposed notches, one narrow (3a) and one wide (4a). The cutting disk has a flat side and a curved side. The center of each internal notch (3a) (4a) is between respective consecutive blades. This feature defines this as a type "A" cutting disk.

Figures 2, 12A:
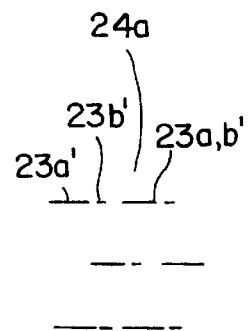

FIG. 2 illustrates a side view of a type "B" cutting disk. The type "B" cutting disk (1b) shown is a thin annulus whose external circumference is comprised of a symmetric series of cutting blades (2b). The internal circumference of the cutting disk contains two diametrically opposed notches, one narrow (3b) and one wide (4b). The cutting disk has a flat side and a curved side. The angular orientation between the external circumference blades and the internal circumference notches shown has the internal notches (3b) (4b) corresponding to external blades. It is this feature which defines this as a type "B" cutting disk.

Figure 2B:
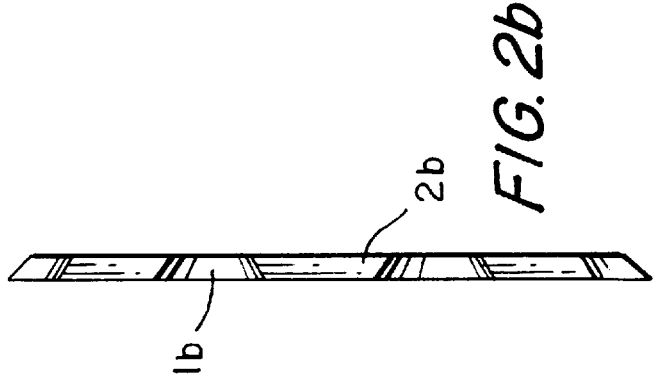
FIG. 2 illustrates a side view of a type "B" cutting disk.
Figure 2A:
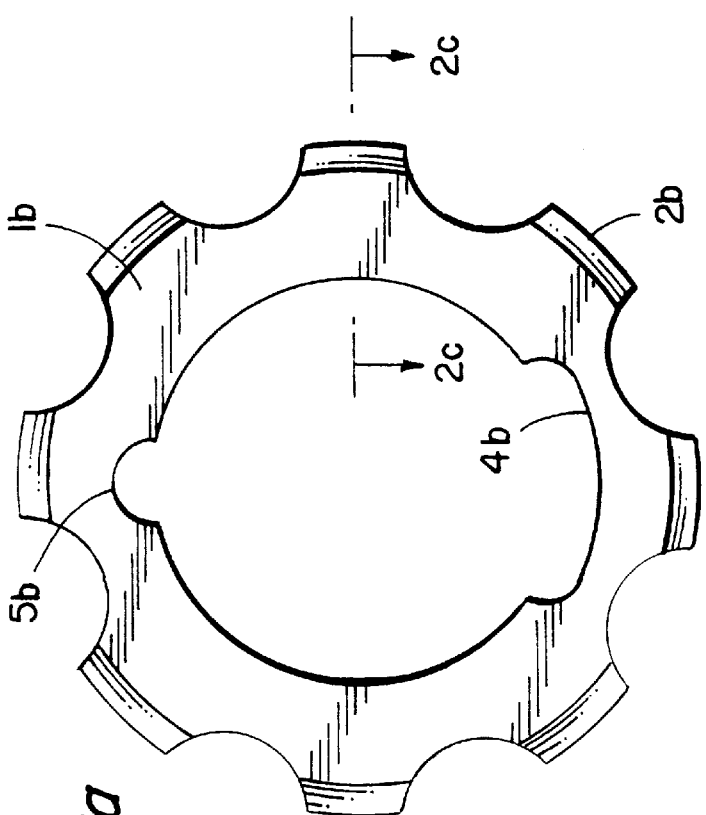
Figure 2C:
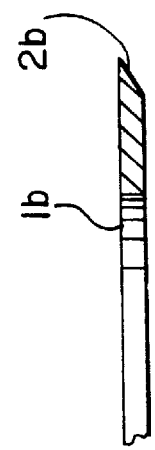
Figure 3:
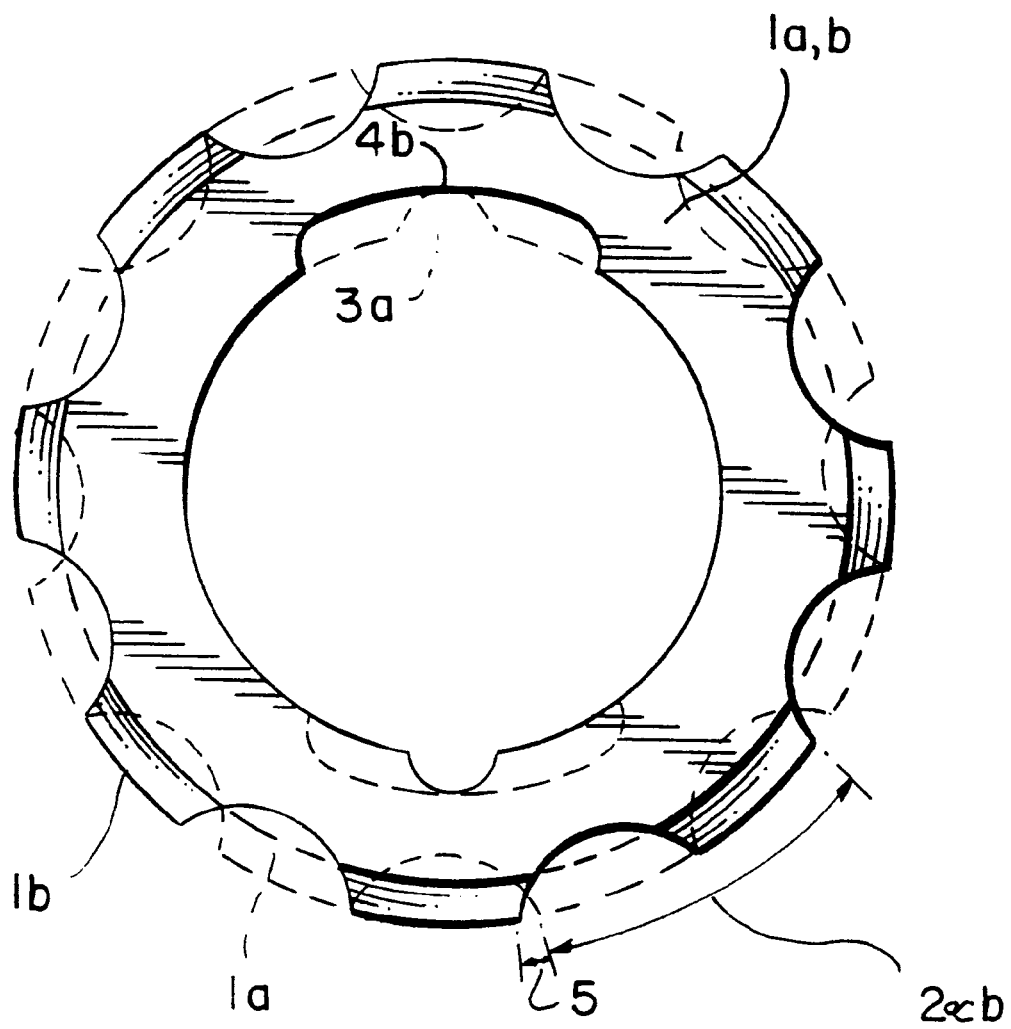
FIG. 3 illustrates a side view of a type "A" and type "B" cutting disk pair.

FIG. 3 illustrates a side view of a type "A" and type "B" cutting disk pair (1ab), where the dashed line is a type "A" cutting disk (1a) and the solid line is a type "B" cutting disk (1b). The relative angular orientation between the pair of cutting disks is determined by the location of the narrow internal notch (3a) on the type "A" disk with respect to the wide internal notch (4b) on its mate. The type "B" disk, by its rotation with respect to the type "A" disk, changes the length of the paired blades (2ab) on the external circumference of the cutting disk. Thus, the relative positions of the notches in the type "A" disk with respect to the notches in the type "B" disk in the pair of cutting disks modulates the degree of the external disk pair which is cutting blade (2ab) and that which is space between blades (5). Each incision made on the skin graft sample then comes from an effective cutting blade (2ab) which has a blade contribution from one or both of the cutting disks in the pair. The rotation of the disk pair over the moving carrier plate (not shown in this figure) produces an incision series whose incision length to incision skip ratio is determined by the relative lengths of the effective cutting blade to the interval space length between effective cutting blades (5).

FIG. 4 illustrates a longitudinal cross section of the upper drum composite axle (without the cutting disks). The upper drum has a two part axle. The central axle (6) holds along its length a track (7) which protrudes through a long opening in a cylindrical external axle (8). This external axle likewise holds a track (9) which protrudes along its length. Setting and locking (not shown in this figure) the relative angular orientation of the central axle with respect to the cylindrical external axle modulates the relative angular orientation of the two tracks with respect to one another. Thus it is track (7) which can be called the pivoting track and it is track (9) which can be called the fixed track.

Figure 5A:
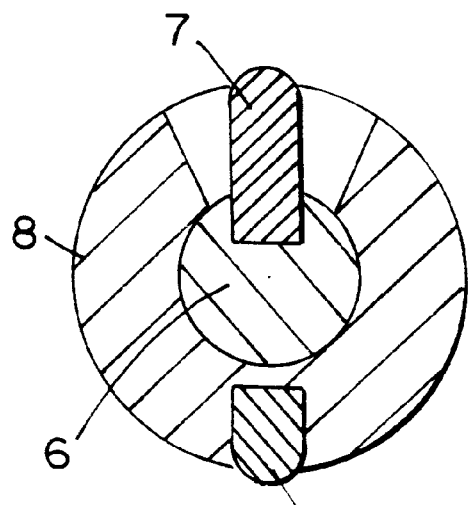
FIGS. 5a and 5b illustrate a transverse cross section of the upper drum (without the cutting disks) at two different angular orientations.
Figure 5B:
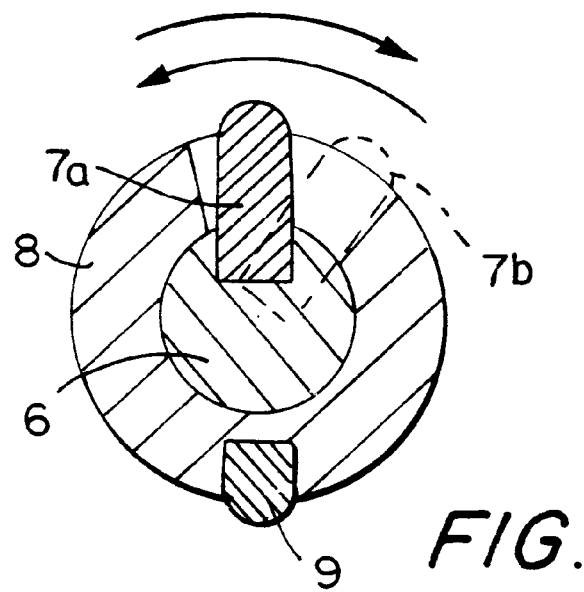

FIGS. 5a and 5b illustrate a transverse cross section of the upper drum (without the cutting disks) at two different angular orientations. In FIG. 5a the central axle (6) holds a track (7) which protrudes through a long opening in a cylindrical external axle (8). This external axle likewise holds a track (9) which protrudes. In FIG. 5b the relative angular orientation of the central axle with respect to the cylindrical external axle is shown for the track (7a) which protrudes through as was shown in FIG. 5a and in a new relative angular orientation (7b) to the other track Changing the relative angular orientation of the central axle with respect to the cylindrical external axle modulates the relative angular orientation of the two tracks with respect to one another (before (7a) (9) and after (7b) (9)). Once the relative angular orientation has been set and locked, the axle pair can rotate as a single composite axle.

Figure 6:
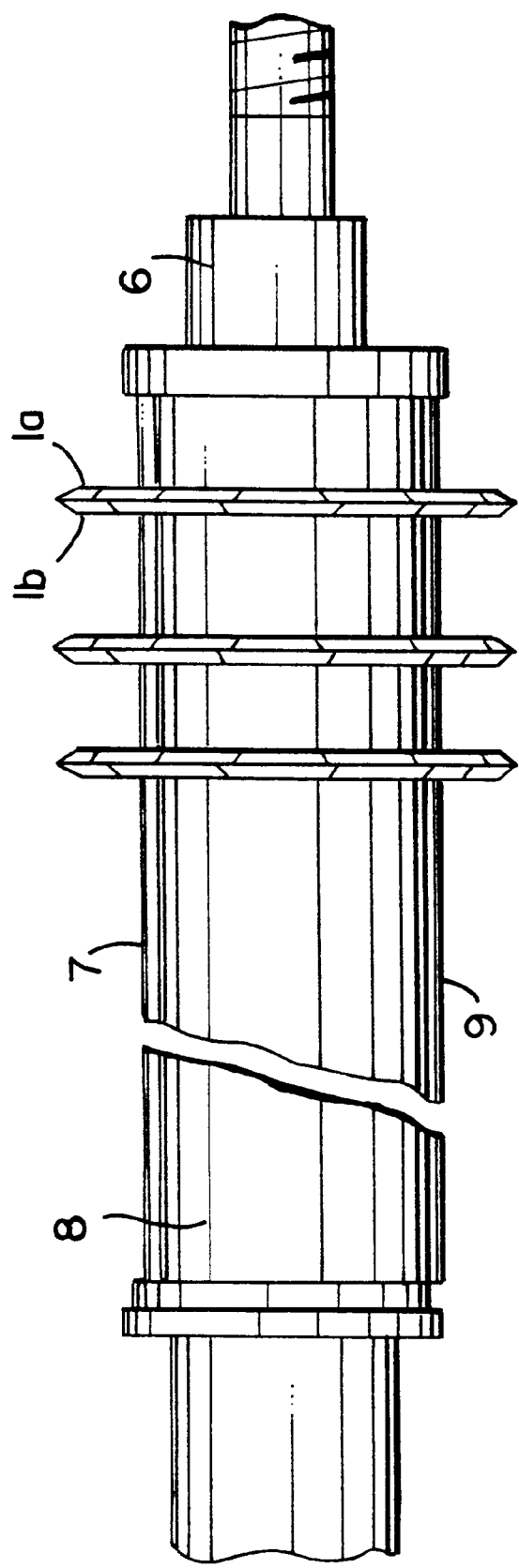
FIG. 6 illustrates a side view of the upper drum having cutting disk pairs aligned on the pair of tracks on the composite axle of the upper drum. (This figure is for illustration only because in reality both sides of every disk touch the sides of the adjacent disks.)

FIG. 6 illustrates a side view of the upper drum having cutting disk pairs aligned on the pair of tracks on the composite axle of the upper drum. (This figure is for illustration only because in reality both sides of every disk touch the sides of the adjacent disks.) Pairs of cutting disks (1a) (1b) are aligned on a pair of tracks (7) (9). These disk pairs can rotate when the composite axle (6) (8) is rotated.

Figure 7:
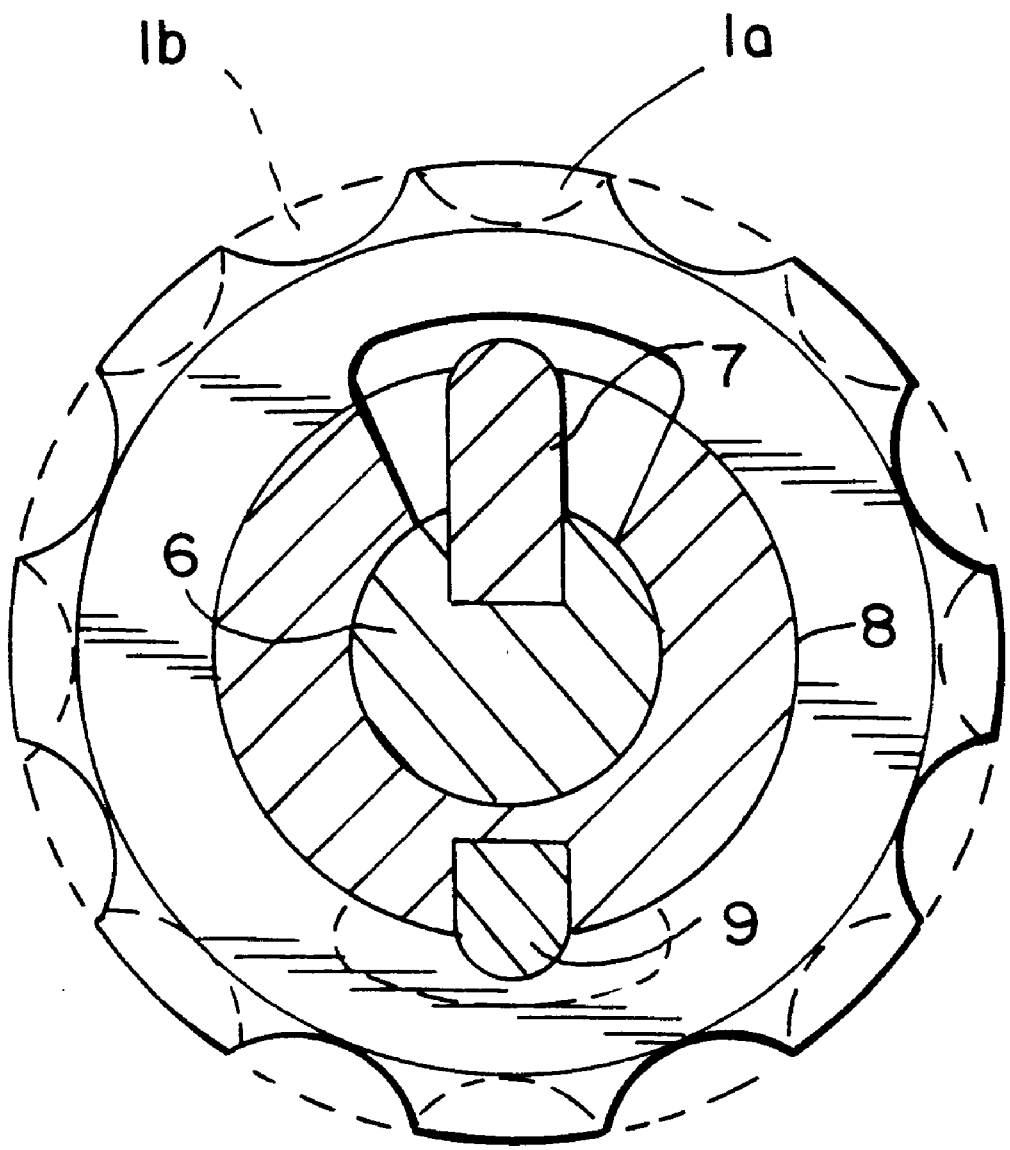
FIG. 7 illustrates a transverse cross section of the upper drum with the disks as described in FIG. 6.

FIG. 7 illustrates a transverse cross section of the upper drum with the disks as described in FIG. 6. A pair ("A" & "B") of cutting disks (1ab), where the dashed line is a type "A" cutting disk (1a) and the solid line is a type "B" cutting disk (1b), are shown on the upper drum. This pair of cutting disks is aligned on a pair of tracks (7) (9). This disk pair can rotate when the composite axle (6) (8) is rotated.

Figure 8:
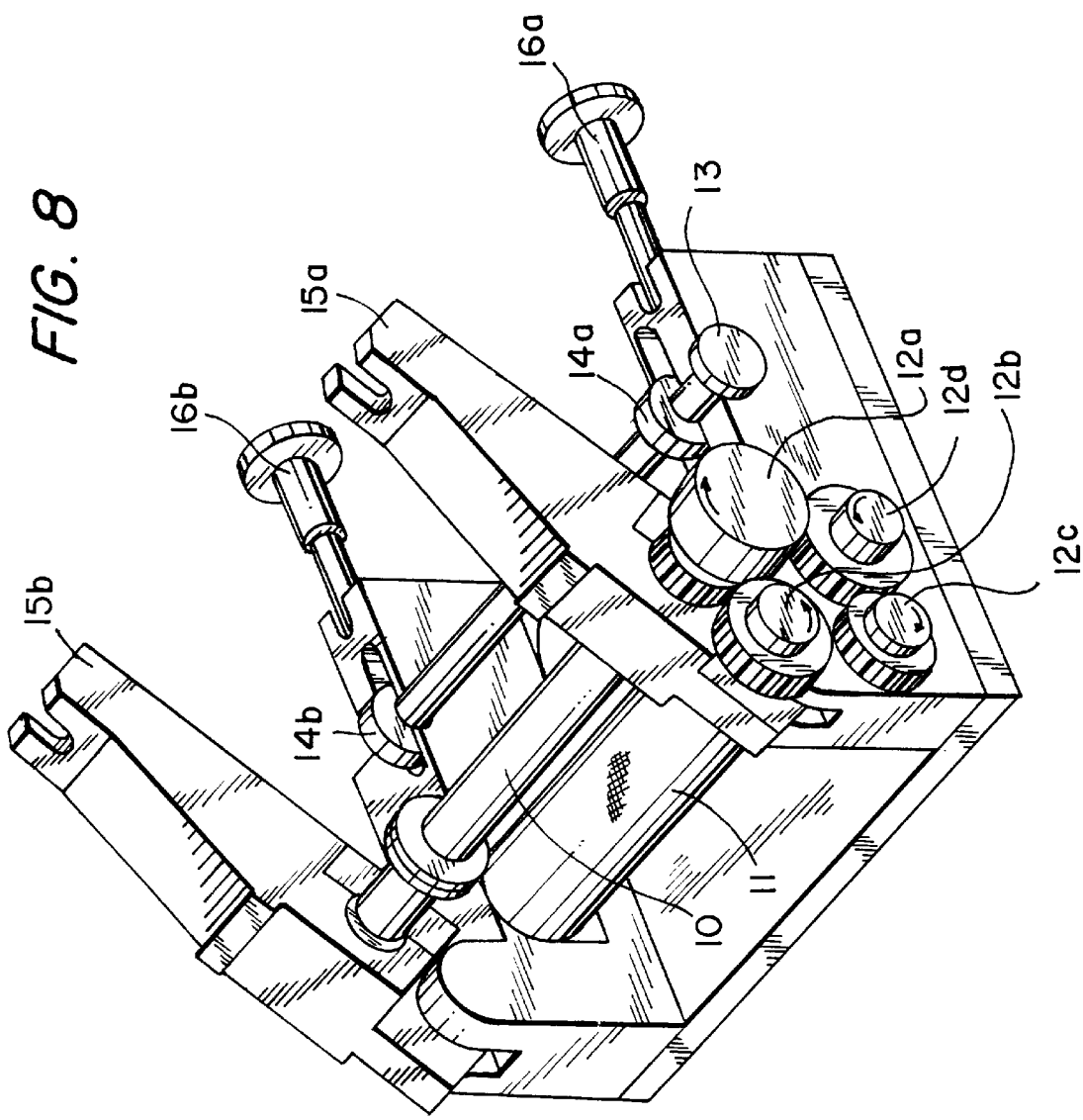
FIG. 8 illustrates an isometric view of the adjustable mesher device.

FIG. 8 illustrates an isometric view of the adjustable mesher device. The upper feeding and meshing drum (10) rotates with respect to the lower feeding drum (11) in a coordinated and synchronous fashion because of the interactions of four toothed wheels (12a) (12b) (12c) (12d), where (10) and (12a) have a common axle and (11) and (12d) have a common axle. These wheels maintain and control the rotations of the two drums even when the adjustable mesher device is set to accept carrier plates of different thicknesses passing between the two drums. Carrier plates can have thicknesses from 0.0 mm to approximately 15.0 mm. setting the device to accept a carrier plate of a predetermined thickness is accomplished by turning a control spool (13) which rotates a pair of eccentric disks (14a) (14b) and these disks determine the accepted carrier plate thickness in that they limit a pair of arms (15a) (15b) from being lowered below this interval thickness. These two arms hold the upper drum and these two arms pivot so as to maintain the coordinated contact between the four toothed wheels. These two arms are connected one to the other by a common handle (not shown in this illustration). Once the two arms are lowered into place against the pair of eccentric disks, the two arms are locked into place by two pivoting pressure adjustment screws (16a) (16b).

Figure 9:
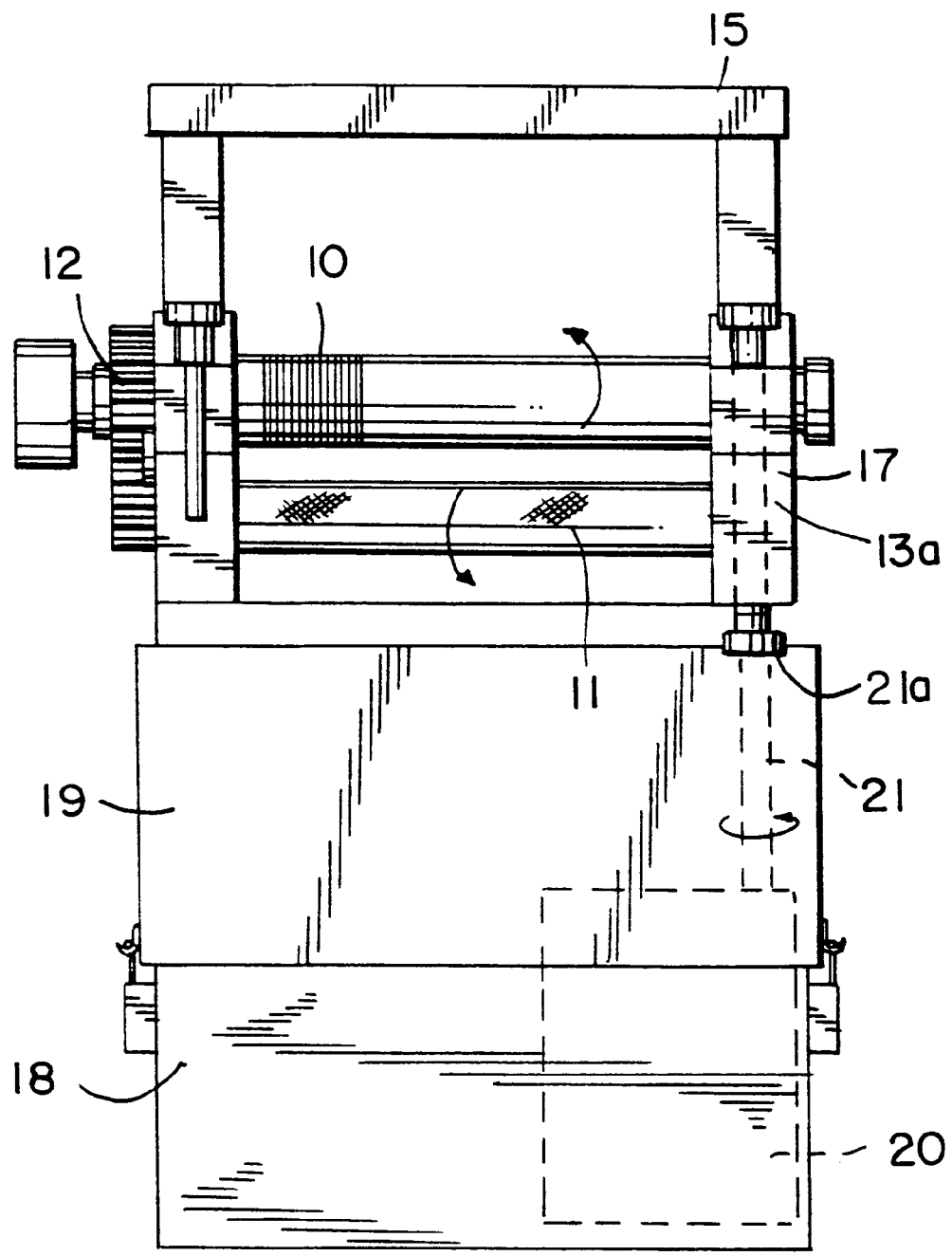
FIG. 9 illustrates a frontal view of the adjustable mesher device integrated with its container and its power source.

FIG. 9 illustrates a frontal view of the adjustable mesher device integrated with its container (18) and its power source (20). There is an adjustable meshing device in which the upper feeding and meshing drum (10) rotates with respect to the lower feeding drum (11) in a coordinated and synchronous fashion because of the interactions of four toothed wheels (12). setting the device to accept a carrier plate of a predetermined thickness is accomplished by turning a micrometric control screw (13a) which limits a pair of arms (here shown joined by a common handle (15)) from being lowered below this interval thickness. The center line of the passage between the two drums through which the carrier plate passes is shown (17). The adjustable meshing device is placed and fitted on the container's cover (19) and completely isolated from the sealable container. In the container is an electric motor unit (20) connected to a rotatable drive shaft (21). The rotatable drive shaft passes through an opening, in the container's cover, containing a rotary shaft packing so as to prevent contact between the operational environment and the container's content. The rotatable drive shaft coupling (21a) is located as an integral part in the container's cover and serves as the means for transferring the rotational power of the motor to the mesher device where the rotational power is divided by the four toothed wheels which in turn rotate the upper and lower drums.

Figure 10:
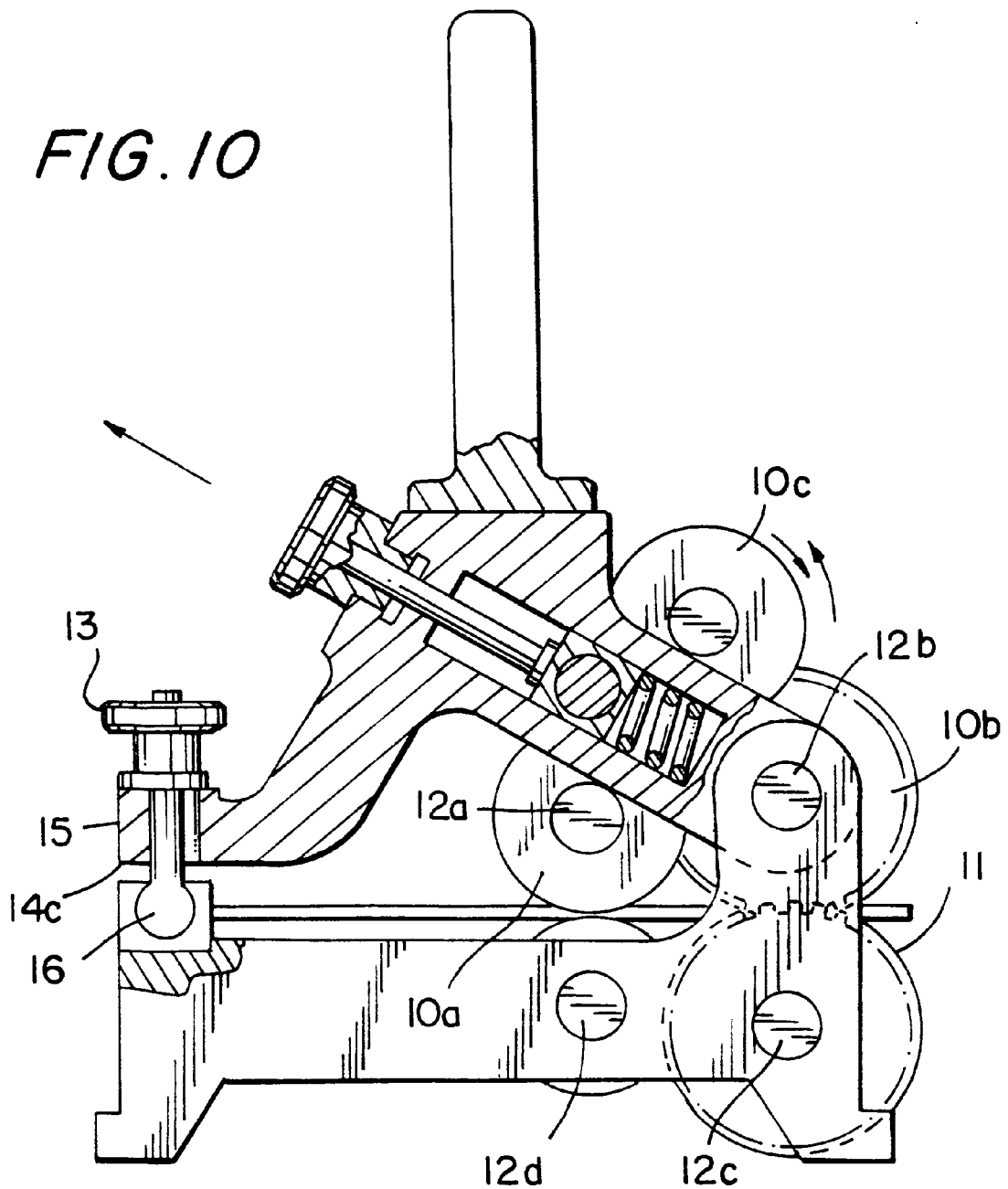
FIG. 10 illustrates a profile of a multi-drum type adjustable mesher device according to the present invention.

FIG. 10 illustrates a profile of a multi-drum type adjustable mesher device according to the present invention. The hereinbefore illustrated single upper meshing and feeding drum has here been replaced with a common holder which holds three parallel meshing drums (10a) (10b) (10c). The meshing drum positioned for operation (10a) is synchronized with the lower feeding drum (11) (partially visible in this illustration) and their rotations are coordinated using four toothed wheels ((12a) (12b) (12c) (12d) not shown) which rotate on the four shown axles where (10a) and (12a) have a common axle and (11) and (12d) have a common axle. Setting the device to accept a carrier plate of a predetermined thickness is accomplished in two steps. Step one is by pivoting a pressure adjustment screw assembly (16) into the upright position where it's upper portion grasps and locks an arm (15) of the upper assembly of the mesher device. The said upper assembly holds the meshing drums and pivots around an axis common to toothed wheel (12d). Step two is by turning a control spool (13) which rotates a micrometric screw (14c). This micrometric screw determine the accepted carrier plate thickness in that it limits the said upper assembly from being lowered below this interval thickness. In this embodiment both the control spool and the micrometric screw are part of a single pressure adjustment screw assembly.

Figure 11:
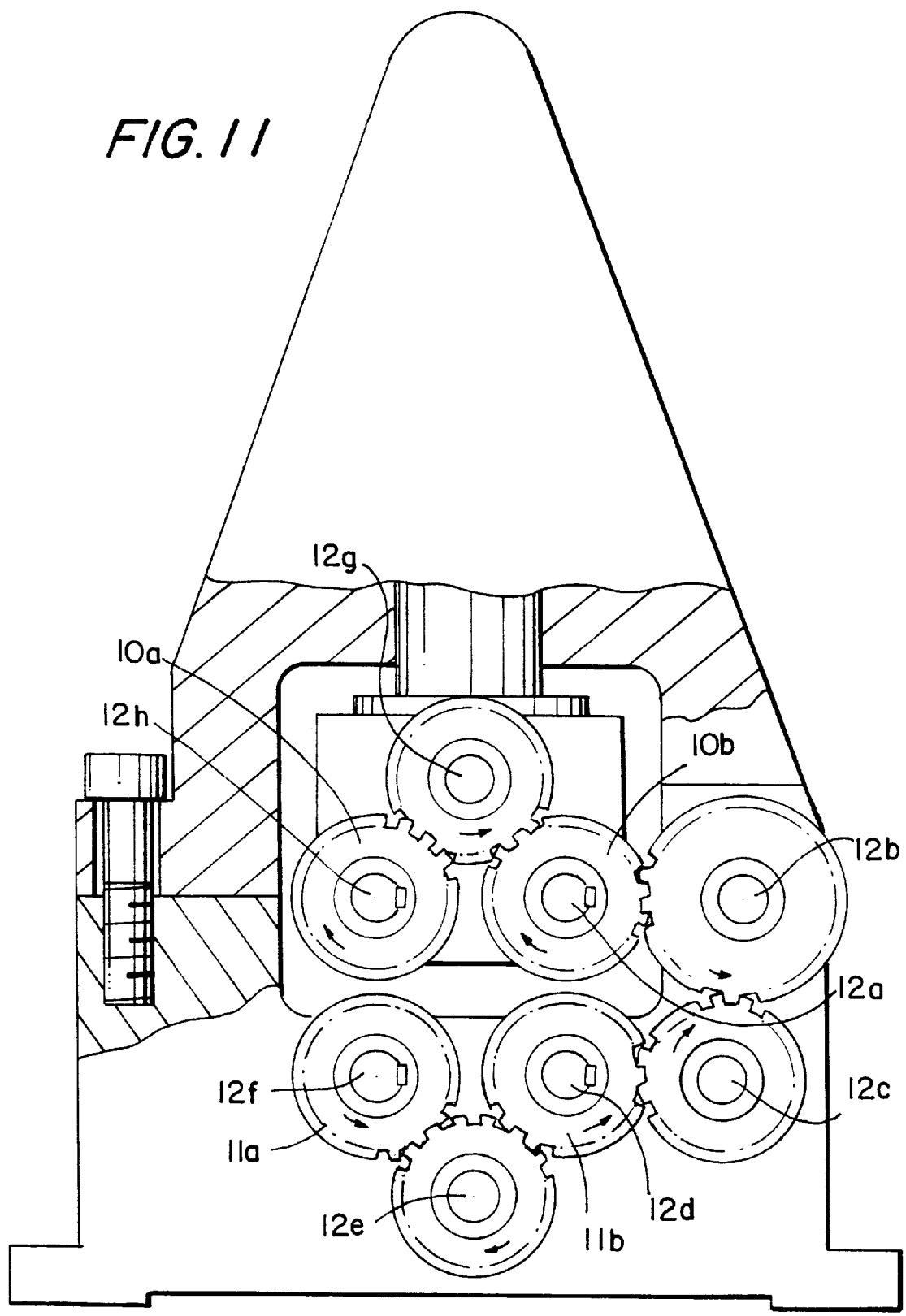
FIG. 11 illustrates a profile of a consecutive parallel meshing drum type adjustable mesher device according to the present invention.

FIG. 11 illustrates a profile of a consecutive parallel meshing drum type adjustable mesher device according to the present invention. Two different consecutive parallel meshing drums (10a) (10b) are juxtaposed against two feeding drums (11a) (11b) and their synchronous rotations are coordinated through eight toothed wheels ( (12a) (12b) (12c) (12d) (12e) (12f) (12g) (12h) not shown) which rotate on eight shown axles where (10a) and (12h) have a common axle, (10b) and (12a) have a common axle, (11b) and (12d) have a common axle, and (11a) and (12f) have a common axle.

Figures 1, 12B:
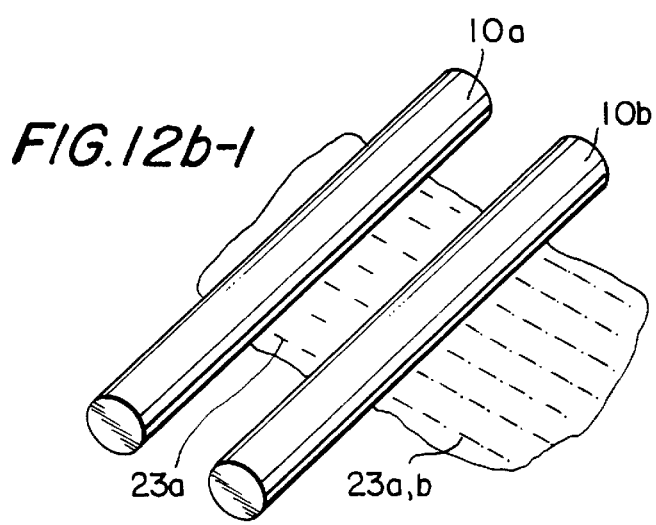
Figures 2, 12B:
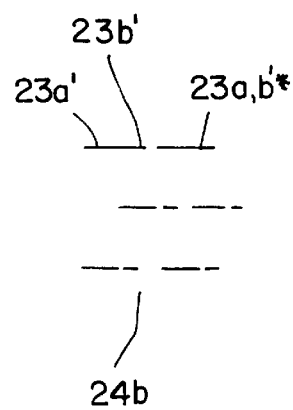

FIGS. 12a and 12b illustrate two oblique views of the incision contributions to a composite meshing pattern as may be produced by a mesher device as illustrated in FIG. 11. In FIG. 12a a piece of skin (22) passes under two different consecutive parallel meshing drums (10a) (10b). Meshing drum (10a) contributes an incision pattern (23a) to the piece of skin passing under it (10a). Subsequently the sections of skin incised with the (23a) pattern passes under meshing drum (10b) which contributes an incision pattern (23b) (not shown separately in this illustration) to the piece of skin passing under it (10b). In an exploded view (24a) of the composite meshing pattern (23ab') the contribution of a single incision (23a') from the first meshing drum is distinguishable from a single incision (23b') from the second meshing drum. Thus a composite meshing pattern (23ab) is produces from the incision contributions of the two different consecutive parallel meshing drums. In FIG. 12b the distance between the two meshing drums seen in FIG. 12a has been shortened changing the relative phase of the contributed incision patterns with respect to one another. A piece of skin (22) passes under the two different consecutive parallel meshing drums (10a) (10b). Meshing drum (10a) contributes an incision pattern (23a) to the piece of skin passing under it (b1a). Subsequently the sections of skin incised with the (23a) pattern passes under meshing drum (10b) which contributes an incision pattern (23b) (not shown separately in this illustration) to the piece of skin passing under it (10b). In an exploded view (24b) of the composite meshing pattern (23ab'*) the contribution of a single incision (23a') from the first meshing drum is distinguishable from a single incision (23b') from the second meshing drum and because the phase relation between the incision contributions has changed, the resultant composite incision 23ab'* is longer than the 23ab' incision produced in FIG. 12a.

FIG. 13 illustrates a profile of a skin detaching rotating brush or a soft serrated cylinder in juxtaposition to and being parallel and along side of a meshing drum. A piece of skin (22) on a carrier plate (24) passes between an upper meshing drum (10) and a lower feeding drum (11) and is incised with a meshing pattern. A skin detaching rotating brush or soft serrated cylinder (25) prevents the skin from becoming wrapped onto the meshing drum and spreads the said skin back onto the carrier plate. If the protrusions of the rotating brush do not extend between the cutting disks but only extend to between the cutting blades on the disks then, rather than preventing the skin graft from becoming wrapped onto the meshing drum, the rotating brush or cylinder/drum would detach the skin graft sample which had become wrapped onto the meshing drum.

I claim:

1. An adjustable skin graft preparation device for producing a predetermined pattern of incisions comprising a plurality of incisions having a predetermined length, said device comprising:

(a) at least one feeding drum rotatably mounted in said device;

(b) a first axle rotatably mounted in said device comprising a plurality of first cutting discs, each said first disc comprising a plurality of circumferentially spaced first cutting edges, said first axle being in substantial parallel arrangement with said at least one feeding drum, said first cutting edges adapted to provide a first pattern of incisions;

(c) a second axle rotatably mounted in said device comprising a plurality of second cutting discs, each said second disc comprising a plurality of circumferentially spaced second cutting edges, said second axle being in substantial parallel arrangement with said at least one feeding drum, said second cutting edges adapted to provide a second pattern of incisions substantially aligned with said first pattern of incisions, wherein each said incision in said predetermined pattern of incisions is contributed by at least one corresponding said first incision and a corresponding aligned said second incision, and wherein said length of each said incision in said predetermined pattern of incisions is determined by the degree of overlap between said corresponding first incision and said corresponding second incision; and (d) means for modulating a disposition of said first axle relative to a disposition of said second axle such as to provide said degree of overlap between said first incisions and said second incisions.

2. An adjustable skin graft preparation device as claimed in claim 1, wherein said first axle and said second axle are comprised in a first meshing drum in coaxial arrangement therein, and wherein said plurality of first discs are intercalated with said plurality of second discs to provide a plurality of pairs of discs comprising one said first disc and one said second disc, wherein each said first disc and each said second disc comprise a substantially flat side, wherein in each said pair of discs said first disc and said second disc are juxtaposed with corresponding flat sides thereof in mutual contact, and wherein said first cutting edges and said second cutting edges thereof are substantially coplanar, such as to provide a plurality of effective cutting blades having an interval space between each pair of adjacent effective cutting blades, said effective cutting blades comprised of a corresponding said first cutting edge and a corresponding said second cutting edge, wherein said length of each said incision in said predetermined pattern of incisions is associated with an effective cutting length of said effective cutting blade.

3. An adjustable skin graft preparation device as claimed in claim 2, wherein said means for modulating a disposition of said first axle relative to a disposition of said second axle comprises modulating a relative angular orientation between said first cutting disc and said second cutting disc of each said pair of discs.

4. An adjustable skin preparation device as claimed in claim 3, wherein said modulation means comprises a first track adapted for axially locking thereon each said first disc of said plurality of pairs of cutting discs, and a second track adapted for axially locking thereon each said second disc of said plurality of pairs of cutting discs, said first axle and said second axle adapted such as to enable the angular orientation of said first track with respect to said second track to be set.

5. An adjustable skin graft preparation device as claimed in claim 4, comprising means for changing the angular orientation of said first track with respect to said second track.

6. An adjustable skin graft preparation device as claimed in claim 4, wherein said first axle constitutes a central axle and said second axle constitutes a substantially coaxial external axle, said central axle comprising said first track, and said external axle comprising said second track, wherein said central axle may be pivoted with respect to said external axle, and therein said first track protrudes through an opening on said external axle.

7. An adjustable skin graft preparation device as claimed in claim 1, wherein said first axle and said plurality of first discs are comprised on a first meshing drum, and wherein said second axle and said plurality of second discs are comprised on a second meshing drum, said first meshing drum and said second meshing drum being in substantial parallel arrangement.

8. An adjustable skin graft preparation device as claimed in claim 7, wherein said means for modulating a disposition of said first axle relative to a disposition of said second axle comprises setting and locking a distance between said first meshing drum and said second meshing drum.

9. An adjustable skin graft preparation device as claimed in claim 7, wherein said means for modulating a disposition of said first axle relative to a disposition of said second axle comprises setting and locking a relative rotational phase between said first meshing drum and said second meshing drum.

10. An adjustable skin graft preparation device as claimed in claim 9, wherein said means for modulating a disposition of said first axle relative to a disposition of said second axle further comprises setting and locking a distance between said first meshing drum and said second meshing drum.

11. An adjustable skin graft preparation device for producing a predetermined pattern of incisions comprising a plurality of incisions having a predetermined length, said device comprising:

a first feeding drum and a first meshing drum rotatably mounted therein;

means for rotating said first meshing drum and said first feeding drum;

said first feeding drum being in substantial parallel arrangement with said first meshing drum, said device adapted to provide a predetermined spacing between said first feeding drum and said first meshing drum;

said first meshing drum characterized in comprising a plurality of pairs of cutting discs coaxially mounted on a shaft, each said pair of cutting discs comprising:

a first annular disc having a substantially flat side and comprising a plurality of circumferentially spaced first cutting edges, and a second annular disc having a substantially flat side and comprising a plurality of circumferentially spaced second cutting edges;

said first disc and said second disc being juxtaposed with corresponding flat sides thereof in mutual contact wherein said first cutting edges and said second cutting edges are substantially coplanar, such as to provide a plurality of effective cutting blades having an interval space between each pair of adjacent effective cutting blades, said effective cutting blade comprised of a corresponding said first cutting edge and a corresponding said second cutting edge, wherein an effective cutting length of said effective cutting blade is determined by the degree of angular overlap between said corresponding first cutting edge and second cutting edge; and modulation means for modulating a relative angular orientation between said first disc and said second disc of each said pair of cutting discs such as to provide a predetermined length ratio between each effective cutting blade length and a length of said interval space between adjacent effective cutting blades in each said pair of cutting discs.

12. An adjustable skin graft preparation device as claimed in claim 11, wherein said modulation means comprises a first track adapted for axially locking thereon each said first disc of said plurality of pairs of cutting discs, and a second track adapted for axially locking thereon each said second disc of said plurality of pairs of cutting discs, said shaft adapted such as to enable the angular orientation of said first track with respect to said second track to be set.

13. An adjustable skin graft preparation device as claimed in claim 12, comprising means for changing the angular orientation of said first track with respect to said second track.

14. An adjustable skin graft preparation device as claimed in claim 12, wherein said shaft comprises a central axle and a substantially coaxial external axle, said central axle comprising said first track, and said external axle comprising said second track, wherein said central axle may be pivoted with respect to said external axle, and wherein said first track protrudes through an opening on said external axle.

15. An adjustable skin graft preparation device as claimed in claim 14, wherein each said first disc comprises at least one first internal notch complementary to said first track for engaging therewith, and wherein each said second disc comprises at least one first internal notch complementary to said second track for engaging therewith.

16. An adjustable skin graft preparation device as claimed in claim 15, wherein each said first disc comprises at lease one second internal notch substantially wider than and diametrically opposed to a said corresponding first internal notch thereof, and wherein each said second disc comprises at least one second internal notch substantially wider than and diametrically opposed to a said corresponding first internal notch thereof.

17. An adjustable skin graft preparation device as claimed in claim 16, wherein a center of said first internal notch of each corresponding said first disc is aligned between a pair of consecutive said first cutting edges.

18. An adjustable skin graft preparation device as claimed in claim 16, wherein a center of said first internal notch of each corresponding said second disc is aligned with a said second cutting edge.

19. An adjustable skin graft preparation device as claimed in claim 11, wherein said first feeding drum is operatively connected for synchronous rotation with said first meshing drum.

20. An adjustable skin graft preparation device as claimed in claim 19, wherein said means for rotating said first meshing drum and said first feeding drum comprises an electric motor unit.

21. An adjustable skin graft preparation device as claimed in claim 20, wherein said electric motor unit is connected to a rotatable drive shaft having a coupling, wherein said electric motor unit and said drive shaft is comprised in a container such as to prevent contact between an operational environment including said device, and internal contents of said container including said electric motor unit and said drive shaft, and wherein said coupling is adapted for transferring rotational power of said motor to said device for rotation of said first meshing drum and said first feeding drum.

22. An adjustable skin graft preparation device as claimed in claim 21, wherein sterilization and aseptic techniques may be applied to said device and said container including said coupling such as to substantially protect a sterile environment including said device and said container from contamination from said contents of said container.

23. An adjustable skin graft preparation device as claimed in claim 21, wherein at least said container and said coupling are autoclavable.

24. An adjustable skin graft preparation device as claimed in claim 21, wherein a non-sterile motor may be transferred and locked into said container using aseptic techniques.

25. An adjustable skin graft preparation device as claimed in claim 21, further comprising a suitable electrical power source selected from the group consisting of a battery, an AC 220-110V source, and an adequate DC source.

26. An adjustable skin graft preparation device as claimed in claim 20, wherein said device is fixed on a cover of said container, and wherein said coupling is an integral part of said cover.

27. An adjustable skin graft preparation device as claimed in claim 20, wherein said rotational power is transferred to said first meshing drum and said first feeding drum via a plurality of toothed wheels.

28. An adjustable skin graft preparation device as claimed in claim 19, wherein said means for rotating said first meshing drum and said first feeding drum comprises a manually cranked ratchet.

29. An adjustable skin graft preparation device as claimed in claim 28, further comprising means for varying said predetermined spacing between said first feeding drum and said first meshing drum.

30. An adjustable skin graft preparation device as claimed in claim 29, wherein said means for varying said predetermined spacing between first said feeding drum and said first meshing drum comprises at least one micrometric screw associated with a corresponding at least one eccentric axle adapted to allow said first meshing drum to be selectively raised or lowered with respect to said first feeding drum.

31. An adjustable skin graft preparation device as claimed in claim 19, further comprising suitable linkage means for enabling said synchronous rotation between said first feeding drum and said first meshing drum to be maintained for a range of predetermined spacings between said first feeding drum and said first meshing drum.

32. An adjustable skin graft preparation device as claimed in claim 31, wherein said range is from about 0.0 mm to about 15.0 mm.

33. An adjustable skin graft preparation device as claimed in claim 31, wherein said linkage means comprises a suitable geared linkage mechanism.

34. An adjustable skin graft preparation device as claimed in claim 11, comprising at least one further said meshing drum, wherein all said meshing drums are carried on a holder in said device, each said meshing drum being rotatably mounted in said holder, said holder rotatably mounted in said device such as to selectively fix each said meshing roller into operating position with respect to said feeding drum.

35. An adjustable skin graft preparation device as claimed in claim 11, further comprising detaching means for detaching meshed skin graft from said first meshing drum such as to substantially prevent said skin from becoming wrapping onto said first meshing drum and for spreading said skin onto a suitable surface.

36. An adjustable skin graft preparation device as claimed in claim 35, wherein said detaching means comprises a fixed comb in parallel arrangement with said first meshing drum.

37. An adjustable skin graft preparation device as claimed in claim 35, wherein said detaching means comprises a brush in parallel arrangement with said first meshing drum.

38. An adjustable skin graft preparation device as claimed in claim 35, wherein said detaching means comprises a serrated drum in parallel arrangement with said first meshing drum.

39. An adjustable skin graft preparation device as claimed in claim 35, wherein said detaching means comprises a soft serrated cylinder in parallel arrangement with said first meshing drum.

40. An adjustable skin graft preparation device as claimed in claim 11, further comprising a second feeding drum and a second meshing drum substantially similar to said first feeding drum and said first meshing drum, respectively, and rotatably mounted in respective parallel arrangement thereto in said device.

41. An adjustable skin graft preparation device as claimed in claim 40, wherein a distance between said first meshing drum and said second meshing drum may be set an locked.

42. An adjustable skin graft preparation device as claimed in claim 40, wherein a relative rotational phase between said relative angular orientation between said first disc and said second disc of each said pair of cutting discs of said first meshing drum, and said relative angular orientation between said first disc and said second disc of each said pair of cutting discs of said second meshing drum may be set and locked.

43. An adjustable skin graft preparation device as claimed in claim 11, wherein said first meshing drum and said first feeding drum are adapted for passing therebetween at least one skin graft sample.

44. An adjustable skin graft preparation device as claimed in claim 11, wherein said first meshing drum and said first feeding drum are adapted for passing therebetween at least one skin carrier plate.

45. An adjustable skin graft preparation device as claimed in claim 11, wherein said first meshing drum and said first feeding drum are adapted for passing therebetween at least one cutting board.

* * * * *